United States Patent
Kim

(10) Patent No.: US 6,986,661 B2
(45) Date of Patent: Jan. 17, 2006

(54) PIN-RETAINED INLAY BRIDGE AND PROCESS OF MAKING AND FITTING SUCH

(76) Inventor: Seung-Ki Kim, 125-12, Songlim 6-dong, Dong-gu, Incheon 401-076 (KR)

(*) Notice: Subject to any disclaimer, the term of this patent is extended or adjusted under 35 U.S.C. 154(b) by 110 days.

(21) Appl. No.: 10/470,837

(22) PCT Filed: Feb. 14, 2002

(86) PCT No.: PCT/KR02/00227

§ 371 (c)(1),
(2), (4) Date: Jul. 30, 2003

(87) PCT Pub. No.: WO02/064054

PCT Pub. Date: Aug. 22, 2002

(65) Prior Publication Data

US 2004/0076925 A1 Apr. 22, 2004

(30) Foreign Application Priority Data

Feb. 13, 2001 (KR) .......................................... 2001-7065

(51) Int. Cl.
*A61C 13/12* (2006.01)

(52) U.S. Cl. ........................................ 433/181; 433/225
(58) Field of Classification Search ................ 433/180, 433/181, 182, 205, 210, 211, 214, 225
See application file for complete search history.

(56) References Cited

U.S. PATENT DOCUMENTS

| 271,476 A | * | 1/1883 | Land .................. 433/199.1 |
| 1,475,808 A | * | 11/1923 | Foster ................ 433/180 |
| 2,314,094 A | * | 3/1943 | Lasky ................ 433/182 |
| 2,910,772 A | * | 11/1959 | Chechik ............... 433/225 |
| 4,661,067 A | * | 4/1987 | Harvey et al. ........... 433/181 |

* cited by examiner

*Primary Examiner*—Cary E. O'Connor
(74) *Attorney, Agent, or Firm*—Dilworth & Barrese LLP

(57) ABSTRACT

The object of this invention is to provide a pin-retained inlay bridge and process of making and fitting such a bridge to a patient. This inlay bridge (100) is firmly fixed to the abutment teeth (200) using a plurality of tapered pins (p) driven into the pinholes (220) of the teeth (200) through the locking holes (121) of the inlays (120) of the bridge (100) after bonding the inlays (120) to the inlay cavities (210) of the teeth (200). This bridge (100) thus minimizes the size of the inlay cavities (210). This bridge thus protects the abutment teeth, and prevents the abutment teeth from being decayed by food which gets stuck between the bridge and the abutment teeth. The present invention also simplifies the process of making and fitting such inlay bridges as well as reduces the operational cost during a dental treatment using bridges.

1 Claim, 10 Drawing Sheets

PRIOR ART

PIN-RETAINED INLAY BRIDGE AND PROCESS OF MAKING AND FITTING SUCH

TECHNICAL FIELD

The present invention relates, in general, to dental prostheses used for replacing one or several teeth and, more particularly, to a pin-retained inlay bridge designed to be retained by abutment teeth using pins when replacing a missing tooth with a metal or ceramic pontic, thus minimizing the size of the cuts formed on the abutment teeth thereby preventing excessive cutting of the abutment teeth, in addition to simplifying the process of making and fitting such a bridge and reducing the operational cost of a dental treatment, and protecting the abutment teeth from harmful effects, such as decaying, for a sufficiently lengthy period of time after fitting the bridge to a patient. The present invention also involves the process of making such a pin-retained inlay bridge and fitting the bridge to a patient.

BACKGROUND ART

In accordance with the normal growth of a man, the first set of teeth are replaced with the second, the man cuts and chews food, speaks precisely, and has good dental appearance with the second teeth. However, when one or more second teeth are damaged due to a variety of dental diseases, such as decayed teeth or gingival diseases, it is very difficult for a patient to eat or speak precisely. Such damaged teeth also cause bad dental appearance, which sometimes impedes the personal relationships of the patient.

It is thus necessary to treat or replace such damaged teeth with dentures in an effort to allow the patients to easily eat, speak precisely and to restore good dental appearance thereby allowing the patients to restore self-confidence in their personal relationships. In recent years, dental treatment has been performed to maintain dental health and allow patients to overcome an unsettled feeling caused by damaged teeth. It is necessary for the dentures to precisely meet the different dental conditions of patients. The objective of the dentures is to partially or fully restore the natural function and beauty of the teeth.

As is known to those skilled in dentistry and prosthodontia, dentures are the dental prostheses used for replacing one or several of the teeth when the teeth and the surrounding tissues are damaged or missing. Such dentures are called "artificial teeth" or "false teeth". In a general sense, the dentures mean consist of dental prostheses with pontics, and involve partial dentures, full dentures and dental bridges. In a detailed description, the dentures include dental caps, crowns, bridges, veneers, inlays, onlays, peripheral caps and crowns, and inlay bridges retained on abutment teeth when replacing one or more missing teeth with pontics arranged on the remaining roots of the missing teeth.

As described above, the dentures are typically classified into three types: bridges, partial dentures and full dentures. The bridges are used for replacing one or more missing teeth with pontics, are retained by crowns which are fitted to the abutment teeth around where a teeth is missing and are connected to the pontic crowns. The conventional bridges are classified into fixed and removable types. The fixed bridges are semi-permanently retained in the dental cavities, and variously classified in accordance with their sizes, production and uses.

Different from such bridges, the partial dentures are artificial teeth, which are retained by natural teeth and the surrounding tissues to restore the function of the damaged teeth when one or more teeth and the surrounding tissues are damaged. The partial dentures take the place of the damaged teeth and restore a good dental appearance.

Full dentures are artificial teeth, which are made using a variety of materials and fitted to patients having no natural teeth. The full dentures are thus called "final treatment and final dentures for dental patients. Using such a full denture, a patient can cut and chew food, speak precisely, and have a good and natural dental appearance. The full dentures are designed, made and fit to patients without adversely-affecting the patient's soft tissues.

The present invention relates to such a fixed bridge, which is used for replacing one or more missing teeth with pontics retained by crowns fitted to the abutment teeth around the missing teeth. The fixed bridge restores the food cutting and chewing function of the teeth, and corrects bad pronunciation, as well as providing a natural dental beauty. Some conventional examples of such bridges are briefly described below.

An example of such conventional bridges is a crown bridge. The crown bridge consists of a pontic crown integrated with two caps, which have the same shape as that of natural teeth. The caps of the crown bridge are fitted over the abutment teeth around the missing tooth, thus restoring the function of natural teeth.

As shown in FIG. 6, in order to fit such a crown bridge to a patient, two natural teeth 200 around a missing tooth are each cut by 2~3 mm at their top surfaces and 1~3 mm at their side surfaces, resulting in the two abutment teeth 200 being cut by about ⅓ of their original sizes. An impression is then taken of the teeth and the surrounding tissues. After taking the impression, a crown bridge is made of dental ceramic or dental acrylic resin through a casting process on the basis of the impression. The crown bridge has a pontic with two crown-type caps, and the two caps are fitted over the abutment teeth 200 such that the pontic replaces the missing tooth. In such a case, the dental ceramic or dental acrylic resin provides shape and color almost equal to that of the natural teeth.

Such a conventional crown bridge is advantageous in that it is easily made and fitted to a patient, and has a low treatment cost. However, this crown bridge is problematic in that it requires the cutting of natural teeth around a missing tooth to provide abutment teeth, over which the crown-type caps of the bridge are fitted. Dental treatment using such a crown bridge is thus very difficult and may damage dental nerves, resulting in pain to patients while the abutment teeth are cut. In addition, due to the cutting, the abutment teeth may not be effectively used for a normal period of time. The crown bridge easily allows impurities, such as food, to be get stuck between the teeth around the bridge. These impurities are very difficult to remove. Another problem of such a crown bridge resides in that its occlusal surfaces may be holed and/or a gap may be formed between the crown-type caps. In such a case, the abutment teeth and another tooth around the crown bridge are decayed. The crown bridge thus may severely damage the natural teeth.

In an effort to overcome such problems experienced in the conventional crown bridge, there exists the artificial replacement of missing teeth using implants. The implants are dental screws, which are driven into the alveolar bone of the maxilla or mandible of a patient and provide a platform for retaining an artificial tooth in the space of a missing tooth. A representative dental implant has a root shape, and is driven into a predetermined position of the alveolar bone.

When an implant is driven into the alveolar bone, a disposable mount is used as a means of connecting an implant driving tool. In the case of a screw-type implant, the disposable mount is a removable extension of the implant. Such a removable extension has a hexagonal nut-shaped head, which engages with a socket used for driving the implant into a predetermined position of the alveolar bone. After completely driving the implant into the alveolar bone, the disposable mount is removed and discarded. A cover bolt is attached to the top of the implant. After the implant with the cover bolt is driven into the alveolar bone, the tissue of the alveolar bone surrounding the implant grows around the implant for several months, and so the implant is fixed to the tissue.

When the surrounding tissue of the alveolar bone is securely holding the implant, the cover bolt is removed from the implant prior to attaching an impression copying to the implant. An impression of the implant, the teeth around the space and the surrounding tissues is taken, and a denture is made on the basis of this impression. The denture is retained by the abutment teeth using a retaining means. In such a case, the abutment teeth act as a platform fixing the denture to the implant.

However, the artificial replacement of a missing tooth using such an implant is problematic in that it requires three months minimum to about one year maximum to complete the dental treatment, and increases the dental treatment cost. In addition, it is necessary to drive the implant into the alveolar bone while averting the dental nerves and blood veins, and so the implant must be performed by a highly skilled dentist. The artificial tooth fixed by such an implant is inferior in its resistance to lateral impact. The implant may cause severe damage to the maxilla or mandible of a patient when the artificial tooth is laterally impacted. PCT/US1997/12673 (Korean Patent Application No. 1999-7000350) discloses a dental technique designed to overcome such problems experienced in the conventional implant.

On the other hand, Korean Patent Application No. 2000-67885 discloses a dental prosthesis designed to overcome the problems experienced in the conventional crown bridges. As shown in FIG. 7 of the accompanying drawings of this invention, the dental prosthesis consists of an artificial tooth 20, which is provided with a slit 21 extending to ⅔ the total height of the tooth 20. The dental prosthesis also has an inlay 22, which consists of a retaining part 25 and an insert part 27. The retaining part 25 has a plurality of projections 24, and is fixed to an abutment tooth by the projections 24. The projections 24 are downwardly inclined at a predetermined angle. The insert part 27 is inserted into the slit 21 of the artificial tooth 20.

The above dental prosthesis disclosed in Korean Patent Application No. 2000-67885 is advantageous in that it overcomes the problems experienced in the conventional crown bridges and conventional implants. That is the dental prosthesis does not damage the teeth around a missing tooth, and reduces the operational time and cost during a dental treatment, in addition to simplifying the dental treatment. However, it is necessary to separately produce the inlays which secure the artificial tooth to the abutment teeth. It is very difficult to precisely make the prostheses due to errors caused while taking an impression and making the prostheses. The above dental prosthesis is less likely to provide the appearance or function of natural teeth.

In the case of a replacement of a missing tooth using an artificial tooth, it is necessary to form a gap between the lower portions of the natural teeth and the artificial tooth so as to allow an easy removal of impurities from between the teeth. However, the inlay of the above dental prosthesis comes into close contact with the natural tooth (abutment tooth), and so a gap is not formed between the natural tooth and the artificial tooth. This dental prosthesis causes the natural teeth to be decayed by impurities, such as food, which get stuck between the teeth. This ultimately causes severe damage to the abutment teeth and the gum.

DISCLOSURE OF THE INVENTION

Accordingly, the present invention has been made keeping in mind the above problems occurring in the prior art, and an object of the present invention is to provide a pin-retained inlay bridge, which is easily and simply fixed to the abutment teeth to replace a missing tooth of the second teeth with an artificial tooth, thus effectively restoring the function of the natural teeth to allow a patient to cut and chew food, speak precisely and have good dental appearance, and which is also fixed to the abutment teeth without causing the patient any pain.

Another object of the present invention is to provide a pin-retained inlay bridge which is fixed to the abutment teeth while minimizing the cuts of the abutment teeth, thus preventing damage to the abutment teeth.

A further object of the present invention is to provide a pin-retained inlay bridge, which is firmly retained by the abutment teeth using two or three pins, and which is thus not removed from the abutment teeth even when a patient chews highly viscous food, such as gum, wheat-gluten, or candy.

Still another object of the present invention is to provide a process of making and fitting such a pin-retained inlay bridge to a patient.

BRIEF DESCRIPTION OF THE DRAWINGS

The above and other objects, features and other advantages of the present invention will be more clearly understood from the following detailed description taken in conjunction with the accompanying drawings, in which.

FIGS. 2a and 2b are perspective views each showing a pin-retained inlay bridge, according to this invention, and a dental arch missing a tooth before the bridge is fitted to the jaw, in which FIG. 2a shows an inlay bridge according to the primary embodiment of this invention, and FIG. 2b shows an inlay bridge with two inlays each extending laterally according to the second embodiment of this invention;

FIGS. 3a to 3d are views showing a process of fitting the inlay bridge of this invention to a patient, in which:

FIG. 3a shows the step of forming inlay cavities and pinholes on two abutment teeth of the patient;

FIG. 3b shows the step of fixing the inlay bridge of FIG. 2a to the abutment teeth after forming the inlay bridge on the basis of an impression;

FIG. 3c is a sectional view of the inlay bridge of FIG. 2a fixed to the abutment teeth; and FIG. 3d shows the step of fixing the inlay bridge of FIG. 2b to the abutment teeth;

FIG. 4a shows the step of forming inlay cavities and pinholes on two abutment teeth;

FIG. 4b is a sectional view of an abutment tooth of FIG. 4a with an inlay cavity and a pinhole; and FIG. 4c shows the step of fixing the inlay bridge to the abutment teeth;

BEST MODE FOR CARRYING OUT THE INVENTION

Figure 1:
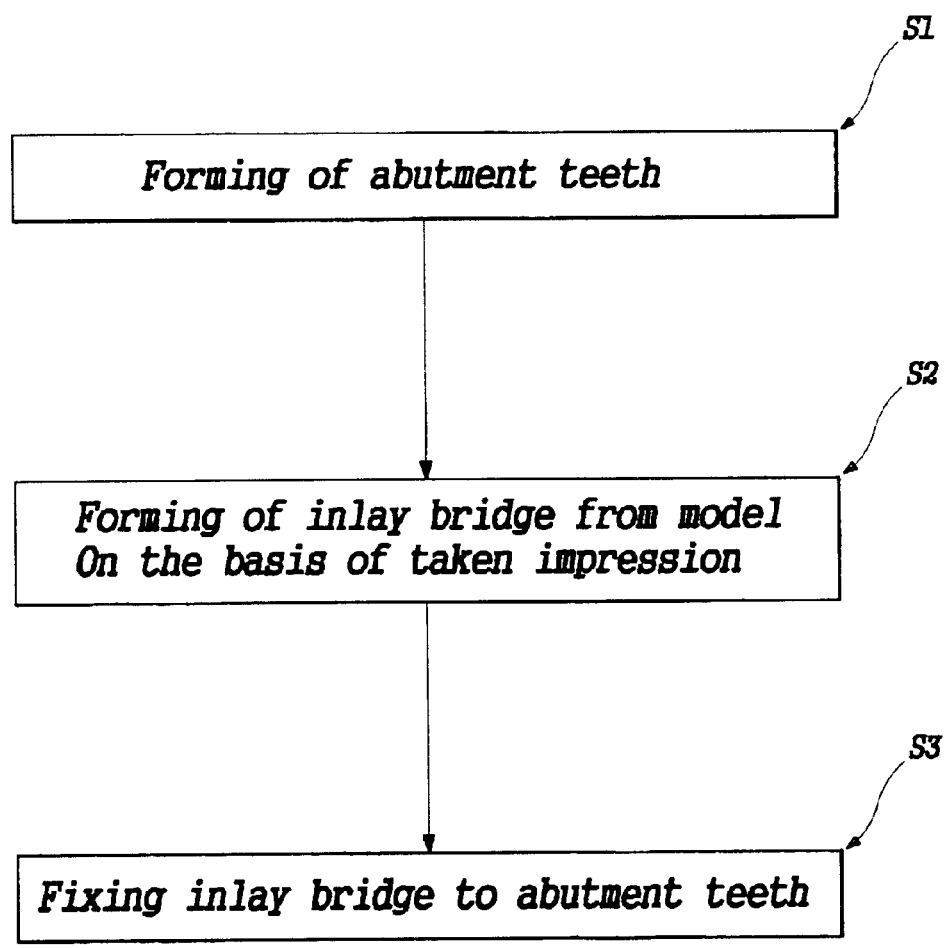
FIG. 1 is a block diagram showing a process of making a pin-retained inlay bridge and fitting the bridge to a patient in accordance with the present invention.

Reference now should be made to the drawings, in which the same reference numerals are used throughout the different drawings to designate the same or similar components.

Figure 2A:
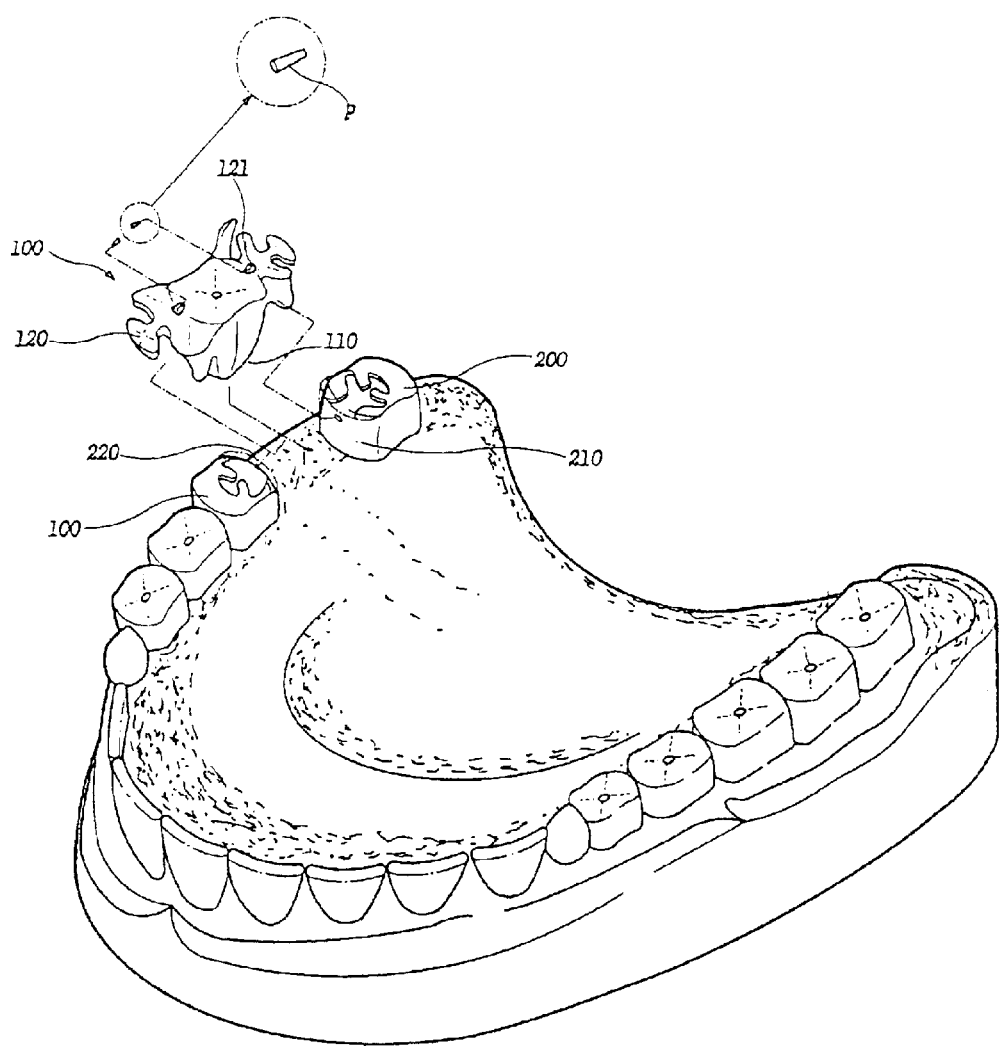
Figure 2B:
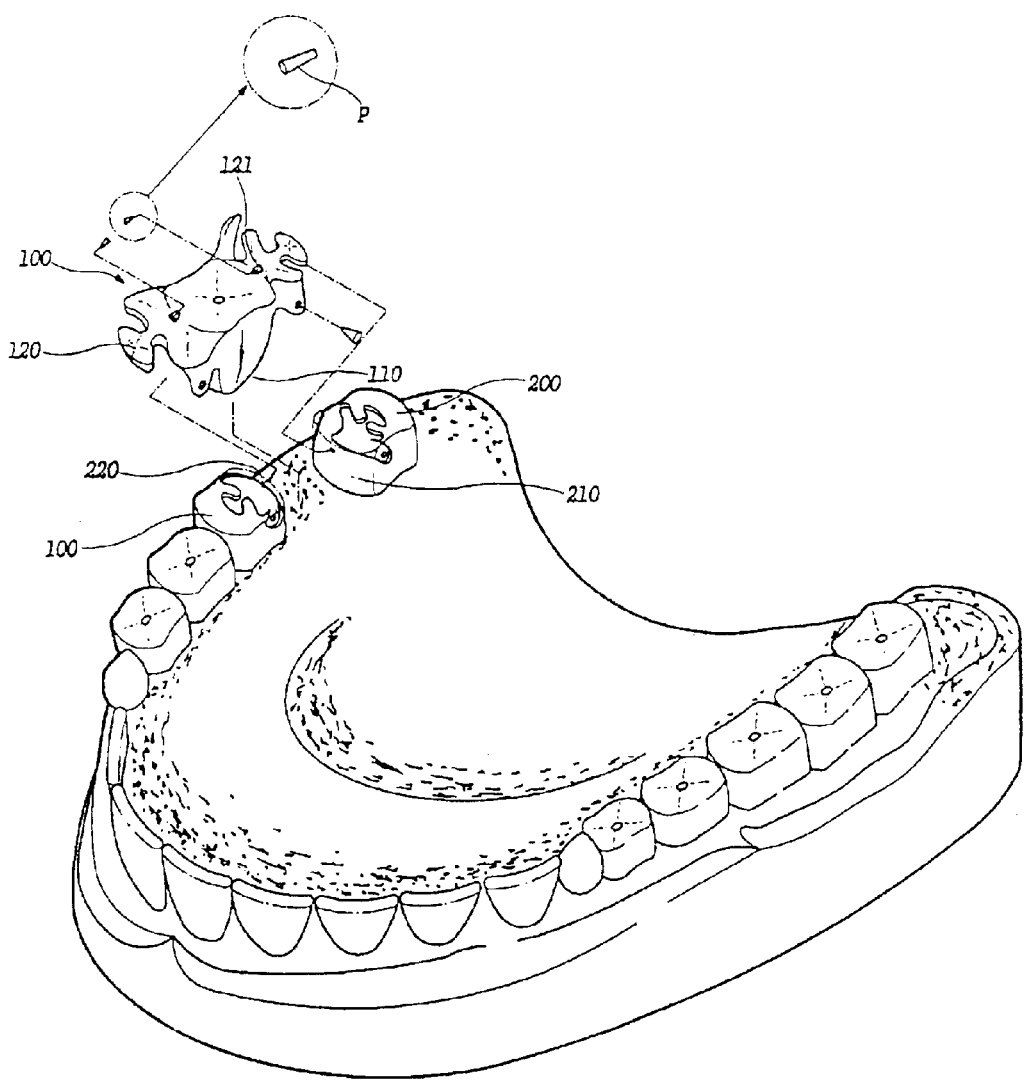
Figure 3A:
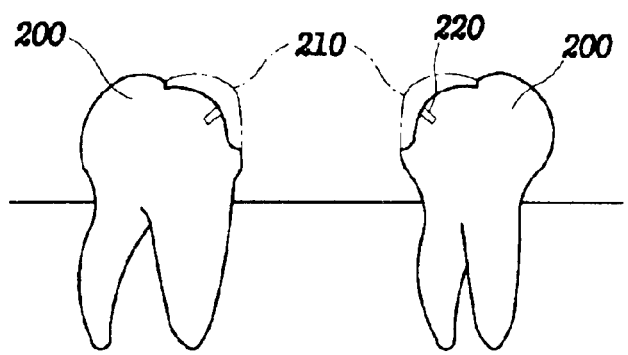
Figure 3B:
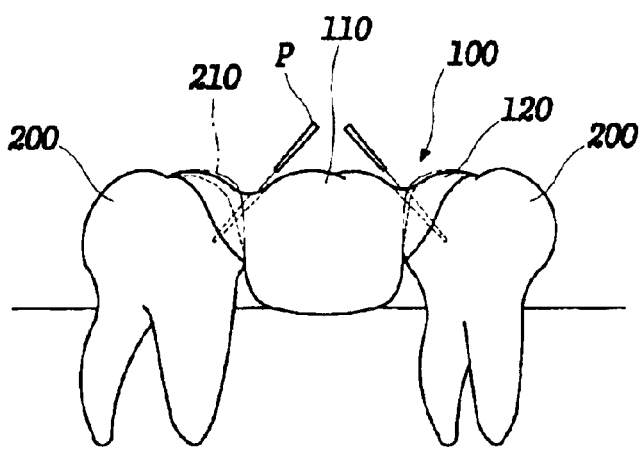
Figure 3C:
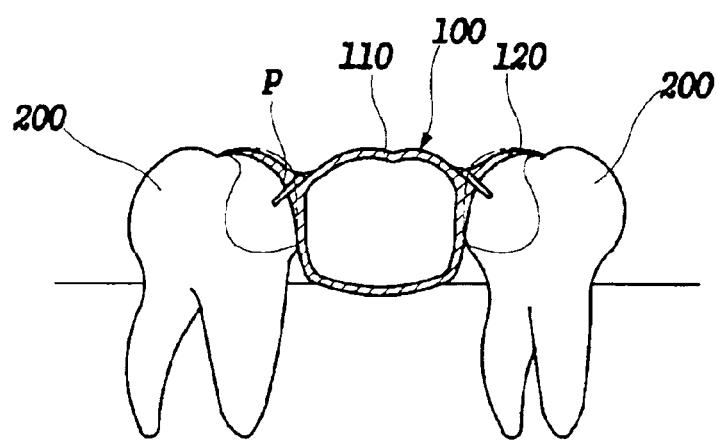
Figure 3D:
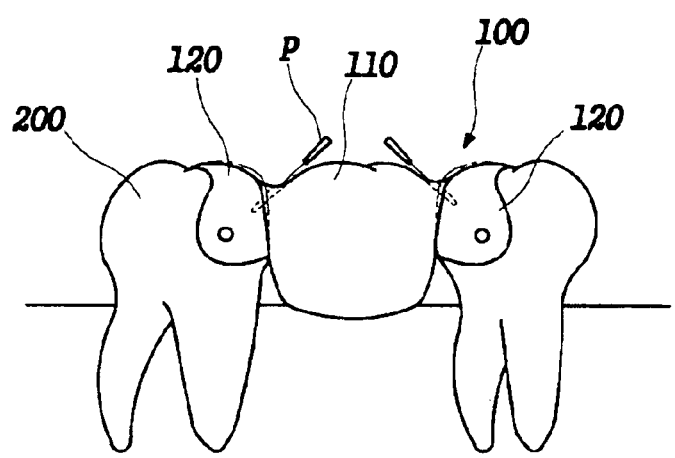
Figure 4A:
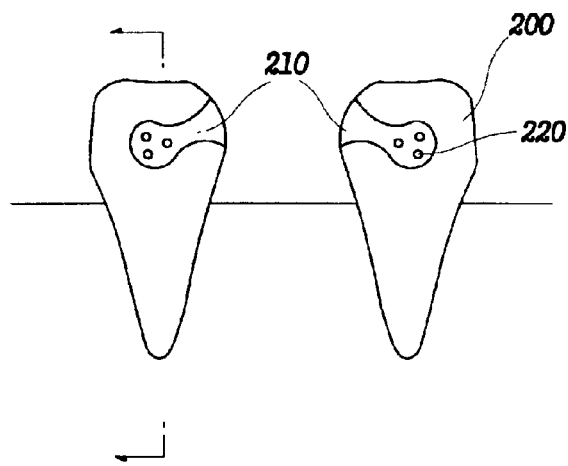
FIGS. 4a to 4c are views which show the fitting of an inlay bridge of this invention to incisors in place of molars of FIGS. 3a to 3d.
Figure 4B:
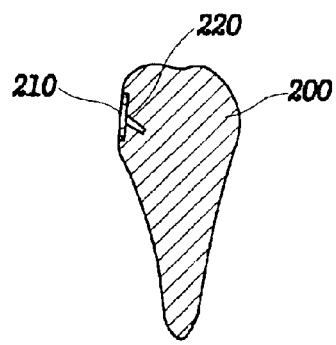
Figure 4C:
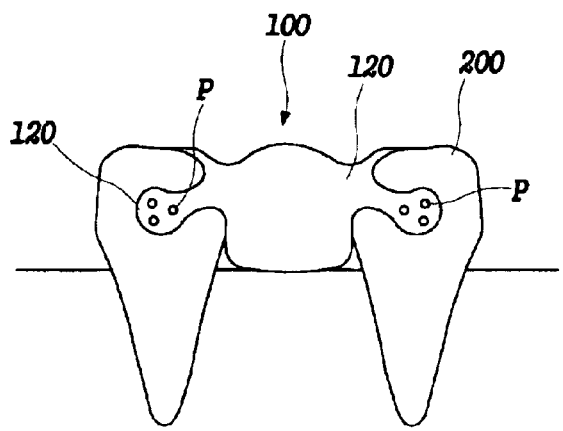
Figure 5A:
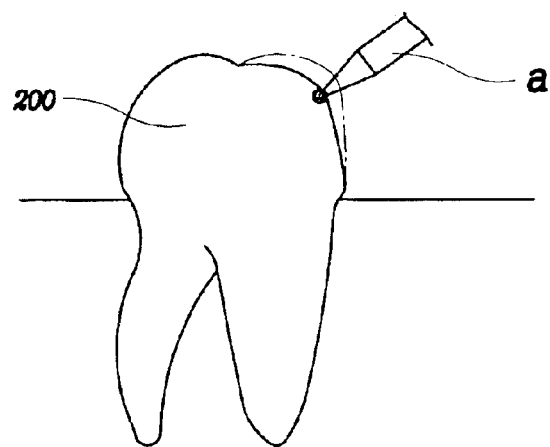
FIGS. 5a to 5c are views showing the process of forming a pinhole at the inlay cavity of an abutment tooth by using a positioning bur, a guide bur and a final forming bur in accordance with the present invention.
Figure 5B:
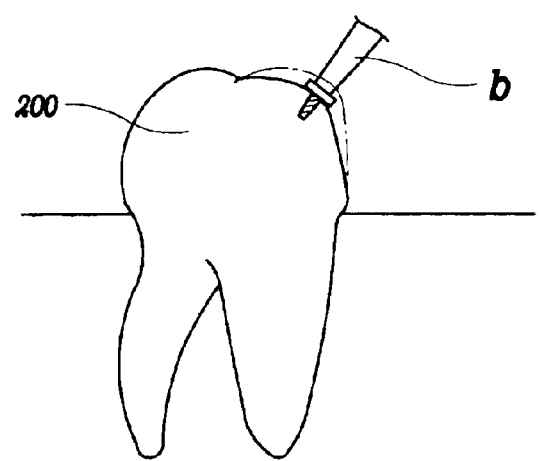
Figure 5C:
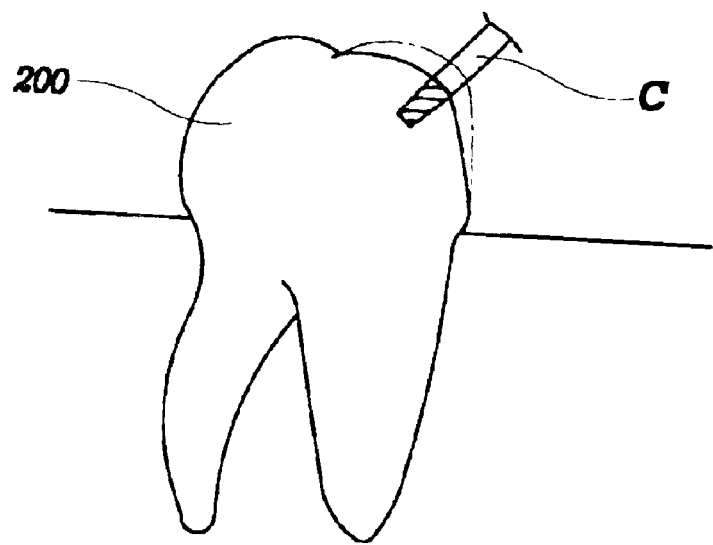
Figure 6:
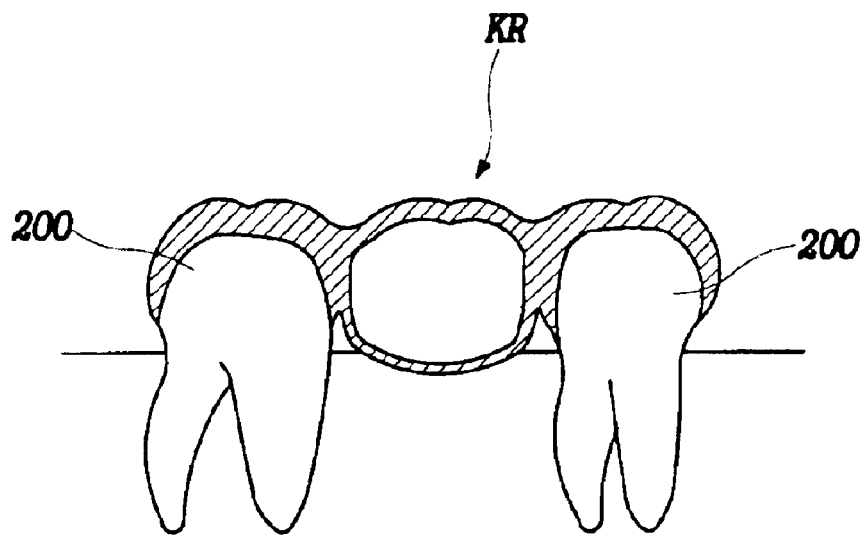
FIG. 6 is a sectional view of a conventional crown bridge fixed to two abutment teeth of a patient.
Figure 7:
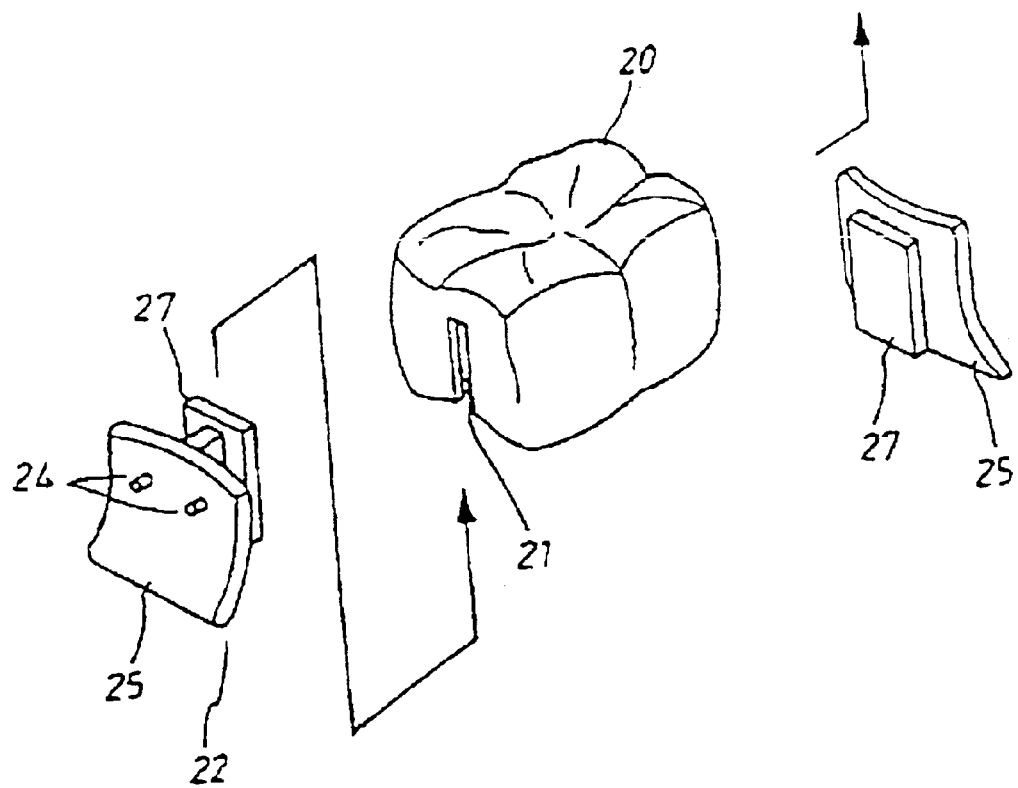
FIG. 7 is an exploded perspective view of a conventional denture according to another embodiment of the prior art.

FIG. 1 is a block diagram showing the process of making a pin-retained inlay bridge and fitting the bridge to a patient in accordance with the present invention. FIGS. 2a and 2b are perspective views each showing the pin-retained inlay bridge according to this invention and a dental arch which is missing a tooth before the bridge is fitted to the jaw. FIGS. 3a to 3d are views showing the process of fitting the inlay bridge of this invention to a patient. FIGS. 4a to 4c are views showing the process of fitting the inlay bridge of this invention to incisors in place of the molars of FIGS. 3a to 3d. FIGS. 5a to 5c are views showing the process of forming a pinhole at the inlay cavity of an abutment tooth sequentially using a positioning bur, a guide bur and a final forming bur in accordance with the present invention;

As shown in the drawings, the present invention provides a pin-retained inlay bridge for replacing a missing tooth, and a process of making and fitting such a bridge to a patient. The process of making and fitting a pin-retained inlay bridge of this invention is described below. In this process, the inlay bridge is used for replacing a tooth missing from the posterior teeth (molars), as an example.

First Step (S1): Forming of Abutment Teeth

This first step carried out involves cutting two natural teeth around a missing tooth (upper or lower jaw), thus forming two abutment teeth for retaining the inlay bridge of this invention.

As shown in FIGS. 2a, 2b, 3a, 3b, 3c and 3d, a dentist forms an inlay cavity 210 on the occlusal and proximal surface of each of two natural teeth 200 around a missing tooth, thus forming two abutment teeth. The inlay cavities 210 of the teeth 200 seat the inlays 120 of an inlay bridge 100 of this invention.

The step of forming such inlay cavities 210 on the abutment teeth 200 is performed before the inlay bridge 100 is fixed to the abutment teeth 200. When such an inlay cavity 210 is formed only on the occlusal surface of each abutment tooth 200 of the posterior teeth, the inlay bridge 100 may be undesirably removed from the abutment teeth 200 due to severe masticatory movement of the teeth. Therefore, in the case of abutment teeth 200 formed around molars, it is desirable to cut the occlusal and proximal surfaces of each abutment tooth 200 to form an inlay cavity 210 as shown in FIGS. 3a to 3d. In such a case, the abutment teeth 200 have an increased inlay retaining ability. That is, the inlay cavities 210 having an enlarged area more firmly retain the inlays 120 of the inlay bridge 100. The depth of each inlay cavity 210 is equal to the thickness of the inlays 120, and so the inlays 120 and the remaining surfaces of the abutment teeth 200 are easily leveled with each other by a burnishing process performed after completely fixing the inlays 120 to the cavities 210. When the inlays 120 are leveled with the surfaces of the abutment teeth 200 as described above, the patient feels comfortable in the same manner as expected from the natural teeth.

The formation of such inlay cavities 210 on the abutment teeth 200 may be carried out in a conventional manner. In addition, it is desirable to form the inlay cavities 210 by finely cutting the abutment teeth 200 such that the inlays 120, integrally extending from both ends of a pontic crown 110 of the inlay bridge 100 and having the same shape as the inlay cavities 120, are seated in and retained by the cavities 210. After forming the inlay cavities 210, a plurality of inclined pinholes 220 of 1~1.5 mm in diameter and 1~1.5 mm in depth are formed at each of the inlay cavities 210, thus completing the formation of the two abutment teeth 200. In such a case, each pinhole 220 is formed on the occlusal surface of the abutment tooth 200 at a position proximate to the pontic crown 110 while being inclined toward the root at an angle of about 45°.

In the present invention, the number of pinholes 220 is set to one, two or three in accordance with the condition of the junction surfaces of the abutment teeth 200 and the pontic crown 220 of the inlay bridge 100, the vital condition of the abutment teeth 200, and the characteristics of the patient's masticatory movement. When the abutment teeth 200 are formed at the molars, the inlay cavities 210 are formed over the proximal surfaces of the abutment teeth 200 as described above. In such a case, the inlays 120 extend to meet the shape of the inlay cavities 210 as shown in FIG. 2b, and are fixed to the cavities 210 by one or more additional pins, thus being more firmly secured to the teeth 200. In such a case, at least one pinhole 220 is inclinedly formed at the cavity area on the proximal surface of the abutment teeth 200.

A brief description of the cross-section of a tooth includes dental pulp which involves the nerves and is positioned at the center of the tooth. The dental pulp is surrounded by the dentin, which is a calcareous tissue. Enamel then surrounds the dentin. The enamel is a calcareous covering of the crown of the tooth. Each pinhole 220 is formed such that it passes through the enamel to reach a predetermined depth of the dentin, thus allowing pins "p" to firmly retain the inlay bridge 100 to the abutment teeth 200 as will be described in detail.

In order to form such pinholes 220 on the abutment teeth 200, a variety of rotary cutting tools, called "burs" in the dentistry, are used. That is, each pinhole 220 is formed as follows: At first, a desired position for a pin "p" is marked on an inlay cavity 210 using a positioning bur "a" as shown in FIG. 5a. This positioning bur "a" has a rounded tip with a diameter of 0.7~1.1 mm. After marking the position of the pinhole 220, a guide bur "b", which has a diameter of 1.2 mm and a length of 1.5 mm, begins to create a hole as shown in FIG. 5b. In such a case, the guide bur "b" enlarges the diameter of the marked position in consideration of the length of the pin "p", thus primarily forming the pinhole 220.

After the primary formation of the pinhole 220, the pinhole is completely formed using a final forming bur "c", which has a tapered shape as shown in FIG. 5c. In such a case, the finally formed pinhole 220 is tapered in a direction from the top to the bottom so as to coincide with the tapered shape of the pin "p".

The final forming bur "c" preferably has a diameter of 1.3~1.7 mm at its tapered tip and a length of 1.5~2.0 mm. The final forming bur "c" is provided with a helical thread around its circumferential surface in the same manner as conventional dental burs, thus feeding chips to the outside of the mouth under the guide of the helical thread during the final step of forming the pinhole 220.

Second Step (S2): Forming of Inlay Bridge from Model on the Basis of Taken Impression After formation of the abutment teeth 200 with both inlay cavities 210 and pinholes 220 through the first step S1, an impression is taken of the patient's teeth and the surrounding tissues. Such an impression is taken by positioning a semisolid material, such as a plastic material, in the mouth to cover the teeth and the surrounding tissues, and hardening the semisolid material for a predetermined period of time. In the present invention, the step of taking the impression is carried out in a conventional manner.

After taking the impression, a plaster mould is formed to produce an artificial denture. A plurality of plastic tubes (not shown) are set in the plaster mould at positions corresponding to the pinholes 220, and a prosthesis model is made using wax. In such a case, the plastic tubes have an inner diameter which is equal to the diameter of the pins "p". The plaster mould with the plastic tubes is used for casting an inlay bridge 100 having a plurality of locking holes 121.

The cast inlay bridge 100 satisfies the clinical requirements of restoring a missing tooth, and has desired mechanical durability, shock resistance, abrasion resistance and good dental appearance. Two inlays 120 integrally extend from both ends of a pontic crown 110 of the inlay bridge 100, and have the same shape as the inlay cavities 120 of the abutment teeth 200 so as to be seated in and leveled with the remaining surfaces of the abutment teeth 200.

Therefore, a plurality of locking holes 121 are formed on the inlays 120 of the inlay bridge 100 at positions corresponding to the inclined pinholes 220 which are formed on the abutment teeth 200 during the first step S1. It is thus possible for a plurality of pins "p" to be driven into the pinholes 220 of the abutment teeth 200 through the locking holes 121 as will be described in the following step.

Third Step (S3): Fixing Inlay Bridge to Abutment Teeth

This third step S3 is carried out to fix the inlay bridge 100, produced from the second step S2, to the two abutment teeth 200 such that the pontic crown 110 of the bridge 100 is positioned in the space of the missing tooth. In order to fix the inlay bridge 100 to the abutment teeth 200, the bridge 100 is positioned on the patient's teeth such that the locking holes 121 formed on the inlays 120 of the bridge 100 are aligned with the pinholes 220 of the abutment teeth 200. After seating the bridge 100 on the patient's teeth as described above, a plurality of pins "p", which have a diameter corresponding to the inner diameter of the pinholes 220 and a length of 3~4 mm, are driven into the pinholes 220 of the abutment teeth 200 after passing through the locking holes 121 of the inlays 120.

Prior to driving the pins "p" into the pinholes 220 to retain the bridge 100 to the abutment teeth 200, it is advisable to firmly attach the inlays 120 of the bridge 100 to the inlay cavities 210 of the abutment teeth 200 using a conventional bonding agent, such as resin cement.

In such a case, the pins "p" are each preferably tapered from the top to the bottom, thus being frictionally compressed to frictionally set in the pinholes 220 when the pins "p" are driven into the pinholes 220 through the locking holes 121. The tapered pins "p" thus act as wedges in the pinholes 220.

The pins "p" are inclinedly driven into the pinholes 220 using a pin driving tool (not shown). Since the inlays 120 of the bridge 100 are attached to the inlay cavities 210 of the abutment teeth 200 using a bonding agent, and the pins "p" are inclinedly driven into the pinholes 220 through the locking holes 121, it is possible to almost completely prevent any undesired removal of the inlay bridge 100 from the abutment teeth 200 regardless of vertical impact and/or lateral impact applied to the bridge 100 during severe masticatory movement of the teeth.

After the inlay bridge 100 is completely fixed to the abutment teeth 200 as described above, the inlays 120 of the bridge 100 and the remaining surfaces of the abutment teeth 200 are leveled with each other by a burnishing process. Therefore, the inlay bridge 100 of this invention allows a patient to feel as comfortable as they would with the natural teeth.

In the above description, the inlay bridge 100 according to the preferred embodiments of this invention is used for replacing a missing molar, as an example. However, it should be understood that the inlay bridge 100 of this invention may be preferably used for replacing a missing incisor in the same manner as that described above without affecting the functioning of this invention. In order to replace a missing incisor with the inlay bridge 100 of this invention, an inlay cavity 210 is primarily formed on the proximal surface of each abutment tooth 200 around the space of the missing tooth as shown in FIG. 4a. Thereafter, a plurality of pinholes 220 are formed at the inlay cavities 210 of the two abutment teeth 200 using a plurality of burs in the same manner as that described for the abutment teeth of molars. Thereafter, an impression is taken of patient's teeth and the surrounding tissues in consideration of clinical information. After taking the impression, an inlay bridge 100 is formed through a molding process using a plaster mould. During the step of forming the inlay bridge 100, a plurality of plastic tubes are set in the plaster mould to form a plurality of locking holes 121 on the inlays 120 of the bridge 100 at positions corresponding to the pinholes 220. After forming the inlay bridge 100, the bridge is fixed to the abutment teeth 200 by primarily attaching the inlays 120 of the bridge to the inlay cavities 210 of the abutment teeth using a bonding agent, such as resin cement, and secondarily driving a plurality of tapered pins "p" into the pinholes 220 through the locking holes 121 using a pin driving tool. In such a case, the tapered pins "p" driven into the pinholes 220 act as wedges, thus firmly fixing the inlay bridge 100 to the abutment teeth 200 of incisors. From the above description, it is noted that the process of making and fitting the inlay bridge for a missing incisor is the same as that described for the inlay bridge for a missing molar.

INDUSTRIAL APPLICABILITY

As described above, the present invention provides a pin-retained inlay bridge and a process of making and fitting such a bridge to a patient. The pin-retained inlay bridge of this invention is easily and simply fixed to the abutment teeth while minimizing the size of cuts of the abutment teeth. This inlay bridge thus effectively protects the abutment teeth, and prevents the abutment teeth from being decayed by food that may get stuck between the bridge and the abutment teeth.

The inlay bridge of this invention is firmly fixed to the abutment teeth using a plurality of pins, and so its removal from the abutment teeth is prevented even when a patient chews highly viscous food, such as gum, wheat-gluten, or candy. Therefore, this inlay bridge allows a patient to perform a masticatory movement of the teeth without being afraid of removal of the bridge from the abutment teeth.

The pin-retained inlay bridge and the process of making and fitting the bridge according to this invention minimizes the size of the cuts formed on the abutment teeth, and prevents an excessive cutting of the abutment teeth, and simplifies the process of making and fitting the bridge, and reduces the operational cost of a dental treatment.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A process of making and fitting a pin-retained inlay bridge, comprising the steps of:

forming an inlay cavity on an occlusal and/or proximal surface of each of two natural teeth around a missing tooth, and forming a plurality of inclined pinholes of 1~1.5 mm in depth at each of the inlay cavities, thus forming two abutment teeth;

taking an impression from clinical information obtained in the step of forming the abutment teeth, and forming an inlay bridge having two inlays respectively fitted in the inlay cavities of the two abutment teeth, with a plurality of locking holes formed on the inlay bridge at positions corresponding to said pinholes of the two abutment teeth; and mounting the inlays of the inlay bridge to the inlay cavities using an adhesive agent such that the locking holes of the inlay bridge are aligned with the pinholes of the inlay cavities, and inserting a pin into each of the pinholes through an associated locking hole, thus fixing the inlay bridge to the abutment teeth.

* * * * *